United States Patent
Pöhlmann et al.

(10) Patent No.: US 7,632,960 B2
(45) Date of Patent: Dec. 15, 2009

(54) PROCESS FOR THE PREPARATION OF NITRIC ESTERS OF MONOHYDRIC ALCOHOLS

(76) Inventors: Jürgen Pöhlmann, Türnicher Strasse 3, D-50969 Köln (Cologne) (DE); Frank Pottharst, An der Mergelskaue 59, D-50226 Frechen (DE); Heinrich Hermann, Donauweg 27, D-50858 Köln (Cologne) (DE); Peter Konieczny, Lerchenweg 2, D-14513 Teltow (DE); Mirko Händel, Weesbacher Strasse 7, D-53819 Neunkirchen-Seelscheid (DE); Jürgen Gebauer, Richard-Wagner-Platz 12, D-53840 Troisdorf (DE)

( * ) Notice: Subject to any disclaimer, the term of this patent is extended or adjusted under 35 U.S.C. 154(b) by 0 days.

(21) Appl. No.: 11/601,975

(22) Filed: Nov. 20, 2006

(65) Prior Publication Data

US 2007/0129563 A1 Jun. 7, 2007

(30) Foreign Application Priority Data

Nov. 21, 2005 (DE) ......... 10 2005 055 794
Nov. 30, 2005 (DE) ......... 10 2005 056 974
Nov. 30, 2005 (DE) ......... 10 2005 057 555

(51) Int. Cl.
C07C 201/02 (2006.01)
(52) U.S. Cl. .......... 558/480; 558/483
(58) Field of Classification Search .......... 558/480, 558/483
See application file for complete search history.

(56) References Cited

U.S. PATENT DOCUMENTS

| 2,618,650 A | 11/1952 | Hinkamp et al. ......... 260/467 |
| 2,734,910 A | 2/1956 | Himkamp et al. ......... 260/467 |
| 2,768,964 A | 10/1956 | Spaeth ......... 260/466 |
| 4,021,498 A | 5/1977 | Alexanderson et al. ..... 260/645 |
| 4,091,042 A | 5/1978 | Alexanderson et al. ..... 260/645 |
| 4,479,905 A * | 10/1984 | Knapp et al. ......... 558/483 |
| 4,496,782 A * | 1/1985 | Carr ......... 568/934 |

FOREIGN PATENT DOCUMENTS

CA 1034603 7/1978

OTHER PUBLICATIONS

R.Andreozzi, R.Marotta, R.Sanchirico, Thermal decomposition of acetic anhydride-nitric acid mixtures, Journal of Hazardous Materials A90, 2002, 111-121.*
Römpp Chemielexikon, $10^{th}$ Ed. Georg Thieme Verlag, Shuttgart/ New York, headword: "Cetan-Zahl" (acetane number), p. 649.
Römpp Chemielexikon, $10^{th}$ Ed. Georg Thieme Verlag, Shuttgart/ New York, headwords: "Nitrierung" (nitration); "Nitriersäuer" (nitrating acid) , pp. 2914, 2915 (1998).
Römpp Chemielexikon, $10^{th}$ Ed. vol. 2, Georg Thieme Verlag, Shuttgart/ New York, headword: "Extraktion" (extraction), p. 1268 (1997).
A.B. Quakenbusch and B.T. Pennington, "The Olin Dinitrotoluene (DNT) Process", Polyurethanes World Congress, pp. 484-488, Oct. 10-13, (1993).
"Extraction liquid-liquid", Kirk-Othmer, Encyclopedia of Chemical Terminology, $3^{rd}$ Ed. vol. 9, John Wiley & Sons, pp. 672-716, (1980).
Health Hazard Evaluation Report No. HETA 82-285-1339, in Chem. Abstracts 102, 190181, 21 pgs., (1985).

* cited by examiner

*Primary Examiner*—Daniel M Sullivan
*Assistant Examiner*—Sudhakar Katakam
(74) *Attorney, Agent, or Firm*—Edward E. Sowers; Brannon & Associates PC

(57) ABSTRACT

The present invention relates to a process for the preparation of nitric esters of monohydric alcohols wherein a monohydric alcohol or a mixture of monohydric alcohols is converted with nitric acid to the corresponding nitric esters under adiabatic reaction conditions in the presence of sulfuric acid.

23 Claims, No Drawings

PROCESS FOR THE PREPARATION OF NITRIC ESTERS OF MONOHYDRIC ALCOHOLS

CROSS REFERENCES TO RELATED APPLICATIONS

This application claims priority to German Patent Application No. DE 10 2005 055 794.5, filed Nov. 21, 2005, and to German Patent Application No. DE 10 2005 056 974.9, filed Nov. 30, 2005, and also to German Patent Application No. DE 10 2005 057 555.2, filed Nov. 30, 2005, entitled "PROCESS FOR THE PREPARATION OF NITRIC ESTERS OF MONOHYDRIC ALCOHOLS". All three of the above references are expressly incorporated by reference herein, in their entirety.

BACKGROUND OF THE INVENTION

The present invention relates to a process for the preparation of nitric esters of monohydric alcohols.

The cetane number (shortly referred to as CN) is a characteristic analogous to the octane number for the ignition performance of a diesel fuel wherein the shorter the time between the moment the fuel enters the cylinder of the engine and the ignition (ignition delay), the higher the value of the cetane number (cf. Römpp Chemielexikon, $10^{th}$ Edition, Georg Thieme Verlag Stuttgart/New York, under headword: "Cetan-Zahl"). For many years already nitric esters of monohydric alcohols as e.g. amyl nitrate, hexyl nitrate, octyl nitrate and their isomers, as e.g. 2-ethylhexyl nitrate, have been used in the function of cetane number improvers for diesel fuels.

Though the mononitrates of these alcohols themselves are not listed as explosives and though they are quite stable, their preparation involves some risks. Sometimes the spent acids from the nitration are not stable and may decompose in an uncontrolled way. Apart from that, during nitration vigorous oxidative decompositions of the product, combined with a so called fume-off, or even an explosion may occur (cf. e.g. Health Hazard Evaluation Report No. HETA 82-285-1339, in Chem. Abstracts 102, 190181 (1985)).

Therefore, various efforts have been made to minimize or eliminate these risks.

For instance, U.S. Pat. No. 2,768,964 discloses a continuous and isothermal esterification of monohydric alcohols with mixed acids (from sulfuric acid and nitric acid) with a water content of 30 to 50% in the presence of urea (1 to 10%) at temperatures of 65 to 110° C. in vacuum. The resulting nitric esters are removed from the reaction mixture by distillation. This method shall prevent an uncontrolled oxidative decomposition of the product caused by the omnipresent nitrose oxides in the reaction mixture.

But this method is rather laborious and with long-chain alcohols such as 1-octanol it produces yields of no more than 52%. Moreover, the high water content in the nitrating acids brings about instable acids.

If the esterification is carried out in a stirred tank reactor or a stirred tank reactor cascade in a continuous way under isothermal conditions and without using urea, it is common in the state of the art to work with mixed acids from nitric acid and sulfuric acid having a water content of 0 to 14% and at temperatures as low as possible, i.e. between −15° C. and maximally 20° C., preferably below 10° C., in the presence of an excess of ca. 5% nitric acid, related to the alcohol to be nitrated. (cf. U.S. Pat. Nos. 2,618,650, 2,734,910 and 4,479,905).

In doing so, the weight ratio of water to sulfuric acid in the final spent acid should not exceed 0.35 in order to prevent the risk of a "fume-off" (cf. U.S. Pat. No. 2,734,910).

Apart from that, the residence times of the reaction mixture in the reactors should be as short as possible, particularly between 0.6 and 15 minutes, preferably between 3 and 6 minutes, to prevent an accumulation of side products resulting from oxidative side reactions.

In the state of the art only a combination of the parameters mentioned above, i.e. low temperatures during nitration, short residence times of the reaction mixture in the reactors and a final spent acid with a weight ratio of water to sulfuric acid below 0.35, allows a comparatively secure, continuous isothermal esterification of primary and secondary alcohols with nitric acid.

These methods, as well, are laborious and require a high degree of monitoring.

Surprisingly it was discovered that the problem described above can be solved if the process is carried out in such a way that the monohydric alcohols are continuously and under adiabatic reaction conditions converted with a mixed acid (a mixture of nitric and sulfuric acid).

Hence, the present invention suggests a method according to the claims and specification. Other advantageous embodiments are described and made the subject of the respective dependent claims.

BRIEF SUMMARY

A process for the preparation of nitric esters of monohydric alcohols is disclosed, wherein a monohydric alcohol or a mixture of monohydric alcohols is converted with nitric acid under adiabatic reaction conditions in the presence of sulfuric acid.

One object of the present disclosure is to describe an improved method for the preparation of nitric esters of monohydric alcohols.

DETAILED DESCRIPTION

For the purposes of promoting an understanding of the disclosure, reference will now be made to the embodiments illustrated in the drawings and specific language will be used to describe the same. It will nevertheless be understood that no limitation of the scope of the disclosure is thereby intended, such alterations and further modifications in the illustrated device and its use, and such further applications of the principles of the disclosure as illustrated therein being contemplated as would normally occur to one skilled in the art to which the disclosure relates.

The subject-matter of the present invention is a process for the preparation of esters of nitric acid (nitric esters) of monohydric alcohols wherein a monohydric alcohol or a mixture of monohydric alcohols is converted with nitric acid under adiabatic reaction conditions in the presence of sulfuric acid. (Apart from nitric acid and sulfuric acid the esterification reagent generally also contains water, usually in varying quantities. This means that usually an aqueous mixture of nitric acid and sulfuric acid is used as esterification reagent.) Usually, the process according to the invention is carried out continuously. Generally spoken, a discontinuous, i.e. batchwise processing is possible as well, though the continuous process is preferred.

Contrary to the processes in the state of the art, according to the invention the conversion is performed not isothermally, but adiabatically, i.e. without any heat exchange with the environment. This means that the reaction can take place at comparatively high temperatures between 10 and 80° C.

In the context of the present invention it has now surprisingly been found that the esterification of monohydric alcohols, as for example amyl alcohol, hexanol, heptanol, octanol, etc. and their isomers with a mixed sulfuric and nitric acid is possible in a continuous way not only—as proposed in the state of the art—isothermally at low temperatures, but can, according to this invention, also be safely carried out adiabatically, particularly within a temperature range between 10 and 80° C., preferably between 10 and 70° C., more preferably between 20 and 60° C., wherein the reaction is preferably performed in a tubular reactor.

Adiabatic reactions with mixed acids from nitric acid and sulfuric acid are generally known in connection with nitro aromatics and are used for example for the preparation of nitrobenzene (cf. U.S. Pat. Nos. 4,021,498 and 4,091,042). But up to now adiabatic reactions have, within the state of the art, not been considered for the preparation of nitric esters.

Especially surprising is the fact that the conversion of the monohydric alcohol or alcohols takes place with a mixed acid from nitric acid and sulfuric acid only, i.e. no additional reagents, especially no urea, are necessary.

Within the present invention preferably primary monohydric alcohols are used. But in principle the conversion of secondary and tertiary monohydric alcohols is possible, as well. According to the present invention as monohydric alcohols, preferably as primary monohydric alcohols, $C_4$- to $C_{12}$-alcohols are used, preferably $C_5$- to $C_8$-alcohols preferably belonging to the group of amyl alcohols, hexanols, heptanols, octanols and isomers and mixtures thereof.

As described above, the reaction, i.e. esterification is carried out specifically within a temperature range between 10 and 80° C., preferably between 10 and 70° C., more preferably within the range of 20 to 60° C.

It is advantageous according to the invention to perform the reaction in a reactor. The entire residence time in the reactor lasts in particular between 0.01 and 30 seconds, preferably between 0.1 and 20 seconds, most preferably between 0.1 and 10 seconds. A tubular reactor has proved especially suitable for the reaction. Such a tubular reactor should include at least one mixing device and at least one volume for residence time, specifically a residence time tube, while in the tubular reactor, particularly in the residence time tube, additional mixing elements may be arranged.

In order to guarantee an efficient course of the process, during the reaction, i.e. during the esterification, a mixing energy of 10 to 1000 J/l (joule/liter), preferably 10 to 300 J/l, more preferably 10 to 100 J/l, should be introduced into the reaction mixture.

The mixture of final spent acid and product resulting after the reaction is generally subject to a phase separation. In doing so it is advantageous to cool the mixture of final spent acid and product down to temperatures between 10 and 30° C., preferably between 15 and 20° C., after it leaves the reactor and before phase separation takes place.

To ensure an efficient course of reaction, the ratio of nitric acid and sulfuric acid in the starting mixed acid should be chosen in such a way that the weight ratio of sulfuric acid to water in the final spent acid (i.e. in the acid obtained after completion of the reaction) is at least 2:1; more specifically it should be in the range between 2:1 and 5:1, preferably between 3:1 and 4.5:1.

Further, to ensure an efficient course of reaction, the ratio of nitric acid to sulfuric acid in the starting mixed acid should be chosen in such a way that the final spent acid resulting after the reaction has a residual content of at least 0.5 weight percentages (wt. %) nitric acid, preferably at least 1 wt. %, more preferably between 1 and 4 wt. % nitric acid. In other words this means that with regard to the alcohols underlying esterification the process is carried out with a stoichiometric excess of nitric acid.

Generally, as starting mixed acid a mixture of nitric acid and sulfuric acid can be used that contains varying amounts of water, particularly a mixture on the basis of a 50 to 99% nitric acid, preferably a 65 to 99% nitric acid, together with a 80 to 99% sulfuric acid, more preferably a 85 to 96% sulfuric acid, and, if necessary with a certain amount of recycled final spent acid (while the recycled final spent acid may particularly have the above mentioned composition).

Part of the final spent acid can be recycled for the preparation of the starting mixed acid. But alternatively it is not obligatory to use final spent acid for the preparation of the starting mixed acid.

According to the invention the monohydric alcohols underlying esterification are, for the purpose to react, fed together with the starting mixed acid, into a mixing zone and subsequently into a tubular reaction zone, in which the reaction is completed. If necessary, additional mixing elements may be arranged in the reaction tube in such a way that the esterification is possible in an optimal way over the whole distance of the reaction tube.

If too little mixing energy is put into the reaction mixture which results in a non-optimal distribution of the sparingly soluble organic phase in the acid phase, the conversion of the alcohol to be esterified will be incomplete after the scheduled residence time and, apart from that, there is a risk that reactive side products may form by oxidative side reactions of the alcohol with the excess nitric acid in the reaction mixture, with the risk of a runaway reaction ("fume-off").

The reaction partners starting mixed acid and monohydric alcohol (to be esterified) may be fed into the reactor in the defined weight ratio for instance by a dosing pump system with especially low pulsation and in such a way that the necessary mixing energy can be introduced.

The process according to this invention achieves a turnover (total yield) of the alcohol to be esterified to nitric ester of more than 99%, preferably at least 99.5%. Other advantages of the process are a minimized reactor volume and, in connection with this, a minimization of the so called "hold-up" in the reactor allowing short start-up times and the possibility to start or interrupt the process within seconds in case of irregularities during the reaction.

Owing to this (short reaction times) and in connection with a quick and effective phase separation, an accumulation of side products in the product and in the final spent acid is reduced to a minimum.

The reactor having at least one mixing zone and at least one reaction zone—these zones may, in particular cases, be identical—is usually not cooled. Consequently, due to the released heat of reaction and the heat of dilution of the mixed acid, the temperature in the reaction mixture rises from the temperature of the mixed acid and the alcohol to be esterified to the defined end temperature. In this process the whole heat of mixing and reaction will be retained in the reaction mixture which serves as "energy store".

The end temperature in the reaction mixture results out of the initial temperature of the reaction partners mixed acid and alcohol and the ratio mixed acid/alcohol and can therefore be exactly adjusted to the properties of the alcohol to be esterified.

Compared with an esterification of the monohydric alcohol performed isothermally and in a continuous mode of operation, e.g. in a stirred tank reactor, the process according to the invention allows, due to the adiabatic reaction with a resulting rise in temperature by 20 to 50° C., for example in a tubular reactor, an acceleration of the conversion of the residual amounts of still unconverted alcohol in the reaction mixture. On the other hand the residence time of the esterification mixture from mixing acid and alcohol in the reactor can be substantially reduced. According to the invention the residence times generally amount to, depending on the alcohol to be esterified and the mixing device applied, 0.01 to 30 seconds, more preferably 0.1 to 20 seconds, most preferably 0.1 to 10 seconds.

In the mixing zone, especially if such alcohols are to be esterified that have only a low solubility in the nitrating acid, the alcohol to be esterified is distributed in the nitrating acid in a way allowing an optimized esterification of the alcohol to be converted.

The required mixing of the reaction partners can be carried out either by means of passive mixing elements or by other means to introduce mixing energy into the reaction mixture.

As mixing elements for example Y-mixers, static mixers, orifice mixers, etc. can be used. The overall mixing energy put into the reaction mixture should be in the range of 10 to 1000 J/l (joule/liter), more preferably 10 to 200 J/l, most preferably 10 to 100 J/l.

After completion of the reaction the nitric ester is separated from the final spent acid. For this purpose the nitrating mixture should be cooled down before phase separation to such a temperature that the solubility of the nitric ester in the final spent acid is reduced to such an extent that a secure storage of the final spent acid is possible without the risk of a postseparation in the acid store caused by cooling down the spent acid. This can be achieved for example by arranging directly after the reactor consisting of mixer and tubular reaction zone an additional cooling zone in which the nitrating mixture is cooled down to 10 to 30° C., more preferably 15 to 20° C.

The separated and cooled down final spent acid can be recycled together with the fresh mixed acid into the process in order to set the required weight ratio between nitrating acid and alcohol to be esterified in such a way that the chosen end temperature of the adiabatic conversion is not exceeded. In other words, the amount of recycled final spent acid can be chosen in such a way that the required end temperature is achieved.

The concentration of nitric and sulfuric acid in the nitrating acid at the end of the reaction is chosen in such a way that the solubility of the esterified alcohol in this acid is minimized, as well as the risk of an oxidative decomposition of the side products dissolved in the final spent acid is kept as low as possible.

For example, a nitrating acid from recycled final spent acid, concentrated sulfuric acid and nitric acid and/or mixtures thereof ("mixed acids") can be used which after the esterification reaction of the monohydric alcohol (i.e. in the final spent acid) has a weight ratio of sulfuric acid to water of at least 2:1, particularly in the range from 2:1 to 5:1, more preferably in the range from 3:1 to 4.5:1, and has after the reaction (i.e. in the final spent acid) a nitric acid concentration of at least 0.5% (wt. %), more preferably at least 1%, most preferably in the range of 1 to 4%.

Apart from the recycled final spent acid, any other acid (nitric, sulfuric and mixed acid) can be used to prepare the nitrating acid used for the esterification of monohydric alcohols, provided the required composition of the final spent acid after completion of the reaction can be achieved. For example by adding 96% sulfuric acid mixed with 65% nitric acid or 96% sulfuric acid mixed with 99% nitric acid or 85% sulfuric acid mixed with 98% nitric acid or mixtures thereof ("mixed acids") to the final spent acid a nitrating acid can be produced out of which the final spent acid is obtained after completion of esterification.

The sulfuric and nitric acids used for preparing a mixed acid and a nitrating acid are not restricted to the concentrations mentioned above. Apart from that, it is possible to dispense with the recirculation of final spent acid as long as the amount of mixed acid used allows absorbing the whole amount of heat evolved during the esterification and dilution of this mixed acid in such a way that the defined end temperature at the end of the adiabatic reaction is not exceeded.

The phase separation of the reaction mixture resulting in product and acid phase may be performed either in static or dynamic separators. The use of dynamic separators (centrifugal separators) is preferred, though, in order to minimize the contact time of the final spent acid with the product and, consequently, the risk that decomposition products from oxidative side reactions with nitric acid may accumulate in the acid and/or the organic phase.

The nitric ester separated from the final spent acid is washed—as usual—in three stages, at first with water, subsequently with an alkali solution and after that with water again. The washing water from the third washing stage is advantageously used in the first washing stage in order to remove the excess acid.

The separation of the washing emulsion after each washing stage may be performed either in a static separator or with the help of dynamic separators (centrifugal separators).

At least part of the separated final spent acid may be circulated. The final spent acid or—in case of recirculation—the excess of final spent acid may be reconcentrated in an SAC plant (SAC=sulphuric acid concentration) in such a way that it may be fed back into the process.

The nitric ester that can be prepared in the process according to the invention may be any nitric ester obtained from any monohydric alcohols, but preferably it is a nitric ester of primary monohydric alcohols which are liquid at a temperature of 0° C. and lead to liquid nitric esters.

Furthermore, the process is not restricted to monohydric alcohols that can be mixed with the nitrating acid or have a still good solubility in the nitrating acid, but is especially applicable for alcohols with poor miscibility and poor solubility in the nitrating acid and final acid, as e.g. 2-ethyl hexan-1-ol, on the example of which the advantage of the described process shall be demonstrated, excluding by doing so any restrictions.

Other embodiments, amendments or variations as well as advantages of the present invention can be easily recognized and realized by the expert taking notice of the disclosed invention, without leaving the limits of the present invention.

The following examples to practice the invention are given to illustrate the present invention, but are not intended to restrict its scope.

EXAMPLES OF THE PRESENT INVENTION

Example No. 1

Nitration with Mixed Acid without Recirculation of Final Spent Acid 1.563 kg/h of 2-ethyl-1-hexanol and 4.567 kg/h mixed acid with 69.2% sulfuric acid, 18.2% nitric acid and 12.6% water and prepared out of 85% sulfuric acid and 98% nitric acid were fed by means of a pump system with low pulsation via a T-tube into the reactor comprised of a static mixer and a reaction zone.

Both feed streams have been tempered to 20° C. The overall residence time in the reactor was 4.0 seconds. The specific energy input was approximately 64 J/l. At the end of the reactor a temperature of 51.5° C. has been reached. The adiabatic temperature rise amounted to 31.5° C. Directly after the reactor the reaction mixture was cooled down to 20° C. After phase separation approximately 2,090 g of the nitric ester of 2-ethyl-1-hexanol were obtained (total yield of the raw product approx. 99%). The composition of the final spent acid (approx. 4.0 kg/h) was: 78.45% sulfuric acid, 1.85% nitric acid and 19.7% water. The ratio sulfuric acid to water amounted to 3.98:1. After the usual 3-stage washing with water, alkali and water again a product was obtained containing 99.6% of the nitric ester of 2-ethyl-1-hexanol and 0.31% impurities, mainly 2-ethyl-1-hexanol.

Example No. 2

Nitration with Mixed Acid and Recirculation of Final Spent Acid

Approximately 0.73 kg mixed acid of the composition 54.5% sulfuric acid, 43.5% nitric acid and 2.0% water, prepared out of sulfuric acid (97.2%) and nitric acid (99%) were continuously mixed with about 2.01 kg/h final spent acid using a low pulsation pump system resulting in a nitrating acid with the composition 71.5% sulfuric acid, 13.3% nitric acid and 15.2% water. Via a T-tube this nitrating acid, together with 630 g/h 2-ethyl-1-hexanol were fed into the reactor comprised of a static mixer and a reaction zone.

The nitrating acid as well as the 2-ethyl-1-hexanol had been cooled down to 20° C. before being mixed. The overall residence time in the reactor amounted to 8.0 seconds. The specific energy input amounted to approx. 36 J/l. At the end of the reactor a temperature of 45.2° C. has been reached. The adiabatic temperature rise amounted to 25.2° C. Directly after the reactor the reaction mixture passed a cooling bath and was cooled down to 20° C. After phase separation ca. 840 g of the nitric ester of 2-ethyl-1-hexanol were obtained (total yield of raw product ca. 99%). The composition of the final spent acid (ca. 2.7 kg/h) was: 77.6% sulfuric acid, 2.4% nitric acid and 20.0% water. The ratio sulfuric acid to water was 3.8:1. After the usual 3-stage washing with water, alkali and water a product was obtained that had a content of 99.5% of the nitric ester of 2-ethyl-1-hexanol and containing 0.4% impurities, mainly 2-ethyl-1-hexanol.

While the preferred embodiment of the invention has been illustrated and described in the foregoing description, the same is to be considered as illustrative and not restrictive in character, it being understood that all changes and modifications that come within the spirit of the invention are desired to be protected.

The invention claimed is:

1. A process for the preparation of nitric esters of monohydric alcohols, wherein a monohydric alcohol or a mixture of monohydric alcohols is reacted with nitric acid in the presence of sulfuric acid in a tubular reactor under adiabatic reaction conditions.

2. The process according to claim 1, wherein the monohydric alcohol is selected from primary monohydric alcohols.

3. The process according to claim 1, wherein the monohydric alcohol is selected from primary monohydric $C_4$- to $C_{12}$-alcohols.

4. The process according to claim 1, wherein the monohydric alcohol is selected from the group consisting of amylalcohols, hexanols, heptanols and octanols as well as their isomers and mixtures.

5. The process according to claim 1, wherein the reaction takes place within a temperature range of 10 to 80° C.

6. The process according to claim 1, wherein the reaction is carried out continuously.

7. The process according to claim 1, wherein the reaction is carried out in a reactor and wherein the time of reaction is from 0.01 to 30 seconds.

8. The process according to claim 7, wherein the overall residence time in the reactor is from 0.01 to 30 seconds.

9. The process according to claim 1, wherein the tubular reactor comprises at least one mixing device and at least one residence time section and optionally additional mixing elements.

10. The process according to claim 1, wherein the overall mixing energy put into the reaction mixture amounts from 10 to 1000 J/l (Joule/liter).

11. The process according to claim 1, wherein the reaction mixture at the end of reaction is submitted to phase separation.

12. The process according to claim 11, wherein after leaving the reactor and before phase separation takes place the mixture of final spent acid and product is first cooled down to a temperature in the range of from 10 to 30° C.

13. The process according to claim 1, wherein the mixing ratio of nitric acid to sulfuric acid in the staffing mixed acid and the concentrations of the used acids in the nitrating acid is chosen in such a way that the weight ratio of sulfuric acid to water in the final spent acid is at least 2:1 and lies within the range of from 2:1 to 5:1.

14. The process according to claim 1, wherein the mixing ratio of nitric acid to sulfuric acid in the staffing mixed acid is chosen in such a way that the final spent acid resulting after reaction has a residual content of at least 0.5 wt % of nitric acid.

15. The process according to claim 1, wherein part of the final spent acid is recycled for the preparation of the nitrating acid.

16. The process according to claim 1, wherein no final spent acid is used for preparing the nitrating acid.

17. The process according to claim 1, wherein the reaction is carried out in such a way that the adiabatic temperature rise, calculated as the difference between the temperatures at the beginning and the end of the reaction, amounts from 20 to 50° C.

18. The process according to claim 1, wherein the reaction is carried out in such a way that the adiabatic temperature rise, calculated as the difference between the temperatures at the beginning and the end of the reaction, amounts from 25 to 40° C.

19. The process according to claim 1, wherein as esterification reagent an aqueous nitric acid/sulfuric acid mixture is used.

20. The process according to claim 19, wherein the aqueous nitric acid/sulfuric acid mixture is made from an 80% to 96% sulfuric acid and a 50% to 99% nitric acid and, optionally, recycled final spent acid.

21. A process of the preparation of nitric esters of monhydric alcohols, wherein a monohydric alcohol or a mixture of monohydric alcohols is reacted with nitric acid in the presence of sulfuric acid under adiabatic reaction conditions, wherein the reaction is carried out in a tubular reactor and wherein the overall residence time in the reactor is from 0.01 to 30 seconds.

22. The process of according to claim 21, wherein the reaction takes place within a temperature range from 20 to 60° C.

23. A process of the preparation of nitric esters of monohydric alcohols, wherein a monhydric alcohol or a mixture of monohydric alcohols is reacted with nitric acid in the presence of sulfuric acid under adiabatic reaction conditions, wherein the reaction is carried out continuously in a tubular reactor within a temperature range of from 20 to 60° C., and the overall residence time being from 0.01 to 30 seconds.

* * * * *